United States Patent [19]
Wu

[11] Patent Number: 5,482,596
[45] Date of Patent: Jan. 9, 1996

[54] MIXED LIGAND CATALYST FOR PREPARING ARYL-SUBSTITUTED ALIPHATIC CARBOXYLIC ESTERS

[75] Inventor: Tse-Chong Wu, Baton Rouge, La.

[73] Assignee: Albemarle Corporation, Richmond, Va.

[21] Appl. No.: 186,933

[22] Filed: Jan. 27, 1994

[51] Int. Cl.$^6$ ..................................................... C07C 51/10
[52] U.S. Cl. ........................................... 562/406; 560/105
[58] Field of Search ............................. 560/105; 562/406

[56]         References Cited
         FOREIGN PATENT DOCUMENTS
   2646792   4/1977   Germany .
         OTHER PUBLICATIONS
Samsel et al., *J. Am. Chem. Soc.*, 107, 7606–7617 (1985).
Irie et al., *Synlett*, Apr. 1991, 265–266.

*Primary Examiner*—Paul J. Killos
*Attorney, Agent, or Firm*—Philip M. Pippenger

[57]            ABSTRACT

A new process for preparing aryl substituted aliphatic carboxylic acids and their esters is provided. A 1-aryl substituted olefinic compound is reacted with carbon monoxide in the presence of water (in aqueous conditions) or an alcohol (in anhydrous conditions) at a temperature between about 25° C. and about 200° C. An excess of several moles of water or of anhydrous alcohol is preferred. An acid such as hydrochloric acid may also be added. As catalyst, a mixture of a palladium compound and optionally a copper compound with a ligand mixture comprising a compound of the formula $(R')_3ZY$ and a compound of the formula $(R")_3Z$ where each R' and R" are the same or different and is alkyl, aryl or substituted aryl, and Z is any atom that has a Pauling electronegativity of between 1.9 and 2.5 and Y is a member of Group VIA of the Periodic Table of Elements.

13 Claims, No Drawings

MIXED LIGAND CATALYST FOR PREPARING ARYL-SUBSTITUTED ALIPHATIC CARBOXYLIC ESTERS

TECHNICAL FIELD

This invention relates to a process for preparing aryl-substituted aliphatic carboxylic acid esters.

BACKGROUND OF THE INVENTION

Among the processes known for preparing 2-(4-isobutylphenyl)propionic acid or esters thereof is that of Shimizu et al. (U.S. Pat. No. 4,694,100, issued September, 1987), who teach the reaction of p-isobutylstyrene with carbon monoxide and water or alcohol in the presence of a palladium catalyst and a mineral acid, e.g., HCl. This patent also teaches the alternative reaction of p-isobutylstyrene with carbon monoxide and hydrogen in the presence of a metal complex carbonyl catalyst to produce 2-(4-isobutylphenyl)propionaldehyde, which is then oxidized to produce the desired product. The preparation of the starting material for this reaction is disclosed as the reaction of isobutylbenzene with acetaldehyde in the presence of sulfuric acid, producing 1,1-bis(4-isobutylphenyl)ethane, which is then catalytically cracked to produce p-isobutylstyrene and isobutylbenzene.

Another process for preparing ibuprofen is that of European Patent Application 284,310 (Hoechst Celanese, published September, 1988), which teaches that ibuprofen can be prepared by carboxylating 1-(4-isobutylphenyl)ethanol with carbon monoxide in an acidic aqueous medium and in the presence of a palladium compound, a phosphine ligand and dissociated hydrogen and halide ions, which are preferably derived from a hydrogen halide. This process has the disadvantage of starting with 1-(4-isobutylphenyl)ethanol, a compound which is not economical to make by known processes.

Gardano et al. (U.S. Pat. No. 4,536,595, issued August, 1985) teach the preparation of alkaline salts of certain alpha-arylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

Alper et al. in *J. Chem. Soc. Chem. Comm.*, 1983, 1270–1271, discloses that alkenes can react with carbon monoxide, water, hydrochloric acid and a mixture of palladium and copper to produce the hydrocarboxylated product, branched chain carboxylic acid. Oxygen is necessary to succeed in the reaction. Subsequently, Alper et al. have disclosed similar catalyst systems, but employing a chiral ligand, as being successful in asymmetric hydrocarboxylation reactions. See Alper et al., PCT Application, WO 91 03,452 and *J. Am. Chem. Soc.*, 112, 2803–2804 (1990).

Also see Japanese Patent Application (Kokai) No. 59-10,545 (Mitsubishi Petrochemical, published January, 1984), which teaches that ibuprofen can be prepared by reacting p-isobutylstyrene with carbon monoxide and water or alcohol in the presence of a palladium (II) catalyst and a peroxide, e.g., cumyl hydroperoxide.

Samsel et al., *J. Am. Chem. Soc.*, 107(25), 7606–7617 (1985), discloses the catalytic epoxidation of various olefins with iodosylbenzene in the presence of catalytically effective amount of certain chromium(III) cations. The reactions are further promoted with pyridine N-oxide and related oxygen donors. Irie et al., *Synlett Letters*, April, 1991, 265–266, is similar but employs chiral (salen) manganese(III) complexes to catalyze asymmetric epoxidations.

The Invention

In the following specification, the meaning of the substituent groups is as follows: "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl, and the like (for the purposes of this definition, "alkyl" is also "aliphatic");

"cycloalkyl" means cyclic alkyl having 3 to 7 carbon atoms and includes cyclopropyl, cyclobutyl, cyclopentyl, cyclohexyl, cycloheptyl and the like;

"substituted aryl" means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, aryloxy including phenoxy and phenoxy substituted with halo, alkyl, alkoxy and the like, haloalkyl which means straight or branched chain alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl and the like;

"alkyl-substituted cycloalkyl" means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, 6-cyclohexylhexyl and the like;

"alkylthio" means a divalent sulfur with alkyl occupying one of the valencies and includes the groups methylthio, ethylthio, propylthio, butylthio, pentylthio, hexylthio, octylthio and the like;

"heteroaryl" means 5 to 10 membered mono- or fused-heteroaromatic ring which has at least one heteroatom and includes those selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl, indolyl and the like;

"substituted heteroaryl" means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

"alkanoyl" means alkanoyl having 2 to 18 carbon atoms and includes, for example, acetyl, propionyl, butyryl, isobutyryl, pivaloyl, valeryl, hexanoyl, octanoyl, lauroyl, stearoyl and the like;

"aroyl" means benzoyl or naphthoyl;

"substituted aroyl" means benzoyl or naphthoyl substituted by at least one substituent such including those selected from the group consisting of halogen, amino, nitro, hydroxy, alkyl, alkoxy and haloalkyl on the benzene or naphthalene ring;

"heteroarylcarbonyl" means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thinoyl, nicotinoyl, isonicotinoyl, pyrazolylcarbonyl, imidazolylcarbonyl, pyrimidinylcarbonyl, benzimidazolylcarbonyl and the like;

"substituted heteroarylcarbonyl" means the above-mentioned heteroarylcarbonyl which is substituted by at least one substituent selected from the group consisting of halogen, amino, nitro, hydroxy, alkoxy and haloalkyl on the heteroaryl nucleus; and includes, for example, 2-oxo-1,3-dioxolan-4-ylmethyl, 2-oxo- 1,3-dioxan-5-yl and the like.

The present invention embraces any salts, racemates and individual optical isomers thereof of the compounds of the following formula (I) having a chiral carbon atom.

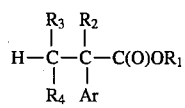

where Ar, $R_1$, $R_2$, $R_3$ and $R_4$ are subsequently defined.

In accordance with the present invention, aryl-substituted aliphatic carboxylic acids or acid esters are prepared by carboxylating an aryl-substituted, olefinic compound with carbon monoxide in a neutral or acidic anhydrous medium containing at least 1 mol of $H_2O$ or a $C_1$ to about $C_8$ linear or branched aliphatic alcohol per mol of olefinic compound at a temperature of between about 25° C. and about 200° C. and a carbon monoxide pressure of at least about one atmosphere in the presence of a mixture of (i) palladium metal or a palladium compound in which the palladium has a valence of 1 or 2 and optionally (ii) a copper compound having a valence of 1 or 2 and a ligand mixture. In place of the aliphatic alcohol, an alcohol equivalent can be used. These include the trialkyl orthoalkonates, dialkyl ketals, alkyl formates, trialkyl borates, or titanium alkoxides. These materials provide a "source of alkoxide ions" as further defined herein. The esters may be readily converted to the corresponding free carboxylic acids or salts by well known conventional methods.

The olefinic-containing compound which is catalytically carboxylated in the practice of this invention has the formula:

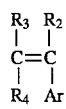

where, Ar is unsubstituted or substituted aryl and $R_2$, $R_3$ and $R_4$ are hydrogen, alkyl, cycloalkyl, substituted or unsubstituted aryl, alkoxy, alkylthio, substituted or unsubstituted heteroaryl, alkanoyl, substituted or unsubstituted aroyl, substituted or unsubstituted heteroarylcarbonyl, trifluoromethyl or halo.

Preferably, in the compounds of formula II, Ar is unsubstituted or substituted aryl, $R_2$, $R_3$ and $R_4$ are hydrogen, $C_1$ to $C_2$ alkyl, substituted or unsubstituted phenyl or trifluoromethyl.

Most preferably Ar is phenyl substituted with alkyl or naphthyl substituted with alkoxy, $R_2$, $R_3$ and $R_4$ and are hydrogen, methyl or trifluoromethyl.

The catalytic carboxylation of the compound of formula II is conducted in an anhydrous medium (in the absence of water) or in an aqueous medium (in the presence of water), at a temperature between about 25° C. and about 200° C., preferably about 25°–120° C., and most preferably about 50°–100° C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere (14.7 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from about 300 to about 3000 psig at the reaction temperature, and most preferred is a pressure from about 400 to about 800 psig. It should be noted that the presence of oxygen is undesirable in the hydrocarboxylation reaction of this invention. Hence, an atmosphere of 100% carbon monoxide is most preferred to carry out this process. Various inert gases can, however, be incorporated in the reaction mass (nitrogen, argon, etc.) the only criteria being that the process should not be slowed to the point of requiring exceptionally long periods to complete the reaction.

The carboxylation is conducted in the presence of at least about one mol of water or an anhydrous aliphatic alcohol per mol of the compound of formula II; however, an excess is preferred in order to assist in driving the reaction to completion. Although there is no real upper limit to the amount of water or alcohol except that imposed by practicality (e.g. the size of the reaction vessel), an amount up to about 100 mols per mol of the compounds of formula II is useful in the process. Further, controlling the amount of water or alcohol used in the process of this invention is advantageous in terms of producing the highest yields. Therefore, an amount from about 2 to about 50 mols of water or alcohol per mol of the compounds of formula II is preferred, and an amount from about 3 to about 24 mols of water or alcohol per mol of the such olefinic compound is most preferred. The product of the reaction is a carboxylic acid (where $R_1$ is hydrogen) or an ester (where $R_1$ is alkyl). These compounds have the following formula:

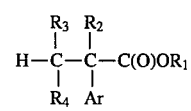

where $R_1$ is hydrogen or alkyl and Ar, $R_2$, $R_3$ and $R_4$ are as previously defined.

Any alcohol which produces an ester of the carboxylic acid may be used in the practice of this invention. In a preferred embodiment, the lower aliphatic alcohols, are used. Examples of the alcohols to be used in this embodiment include methyl alcohol, ethyl alcohol, n-propyl alcohol, isopropyl alcohol, n-, iso- sec-, and tert-butyl alcohols, the pentyl alcohols, the hexyl alcohols, etc. Methyl alcohol is highly preferred, and ethyl alcohol is most highly preferred. Other alcohols, glycols, or aromatic hydroxy compounds may also be used. In the broadest sense, these alcohols provide a source of alkoxide ions for this reaction. However, any other "source of alkoxide ions" may also be used. The source of such alkoxide ions is from a compound selected from the group consisting of $HC(OR_1)_3$, $(R)_2C(OR_1)_2$, $HC(O)OR_1$, $B(OR_1)_3$, $Ti(OR_1)_4$ and $Al(OR_1)_3$ where R is hydrogen or individually the same or different than $R_1$ and $R_1$ is as previously defined.

In a preferred embodiment of this invention, the carboxylation reaction is initiated under neutral conditions, i.e., with no added acid. It can also be performed in the presence of an added acid. When acids are added, such acids include sulfuric acid, phosphoric acid or sulfonic acids. A hydrogen halide acid such as hydrochloric or hydrobromic acid is preferred. The hydrogen halide may be added as a gas phase or as a liquid phase (e.g., in the form of an alcoholic solution). Any concentration may be used. Hydrochloric acid is particularly preferred, at a concentration up to about 10%; more highly preferred is a concentration from about 10% to about 30%. The amount of acid added is such as to provide up to about 40 mols of hydrogen ion per mol of compound of formula II; more preferred is an amount to provide up to about 10 mols of hydrogen ion per mol of compound; the most preferred amount provides up to about 4 mols of hydrogen ion per mol of the compounds of formula II.

The catalytic carboxylation process of this invention is conducted in the presence of a reaction-promoting quantity of i) palladium metal or a palladium compound in which the palladium has a valence of 1 or 2 and optionally ii) a copper compound, with a ligand mixture. The compounds of palladium and (optionally) copper are sometimes referred to as palladium and copper salts. The ligand mixture comprises a compound of the formula $(R')_3ZY$ and a compound of the formula $(R'')_3Z$ where each R' and R'' are individually the same or different and are alkyl, aryl or substituted aryl or is joined together with the group Z to form a heteroaromatic Z is any atom that has a Pauling electronegativity of between 1.9 and 2.5 and Y is any member of Group VIA of the Periodic Table of Elements, including oxygen, sulfur or selenium. Thus, the atom Z can be sulfur, nitrogen, selenium, osmium, phosphorus, arsenic, antimony, mercury, tellurium, germanium and bismuth. In the case of the heteroaromatic compounds, these include bismabenzene, phosphabenzene, pyridine, thiopyran, stelbabenzene, stanmabenzene, 2H-tellurin and the like. Preferably, each R'' is defined as the same as R'.

The most preferred atom for Z is phosphorous. In which case R' and R'' are individually the same or different and are $C_1$ to $C_6$ alkyl, phenyl, substituted phenyl or are joined with the Z to form a pyridine ring. Especially preferred mixtures are those where R' and R'' are the same and are phenyl, and Z is phosphorus.

In the mixture of ligands, a range of from about 1:99 to about 99:1 of $(R')_3ZY$ to $(R'')_3Z$. Preferably, the mixture is from about 80:20 to 20:80, most preferably 60:40 to 40:60. Especially preferred is a ligand mixture composed of equal parts of $(R')_3ZY$ to $(R'')_3Z$.

In one embodiment, palladium and optional copper compounds are inorganic salts and are added as a pre-formed complex of, for example, palladium(II) chloride or bromide, copper(II) chloride or bromide and carbon monoxide or any other similar complex. In a preferred embodiment, active catalytic species are formed in situ by the addition to the reaction mixture of the individual components, i.e., the ligand mixture, the optional copper compound, and a palladium compound such as the inorganic salts of palladium(II) and copper(II). These inorganic salts include the chlorides, bromides, nitrates, sulfates, or acetates. In the most preferred embodiment, the ligand mixture is triphenylphosphine/triphenylphosphine oxide. Copper(II) chloride and palladium(II) chloride are used with such mixture and are added individually or together, either simultaneously or sequentially.

The palladium metal or the palladium and copper compounds can be supported on carbon, silica, alumina, zeolite, clay and other polymeric materials and used as the heterogeneous catalysts.

The amount of (optional) copper and palladium metal or palladium compounds preferably employed is such as to provide from about 4 to about 8000 mols of the compound of formula II per mol of the mixture of metal and salt or of metal salts; more preferred is an amount to provide from about 10 to about 4000 mols of compound of formula II per mol of the mixture; the most preferred amounts provide from about 20 to 2000 mols of the compounds of formula II per mol of the metal salt mixture. The process of this invention is conducted in the presence of at least one mol of ligand mixture per mol of the mixture of the metal and salt or metal salts. More preferably, about 2 to about 40 mols of ligand mixture per mol of the mixture of salts are present, and most preferably about 2 to about 20 mols of ligand mixture per mol of the mixture of salts are used.

The presence of a solvent is not required in the process of this invention, although it may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol, isomers of butanol, isomers of pentanol, etc. Acids and esters may also be used, such as formic or acetic acid or ethyl acetate, etc. When an ester or an alcohol is used as solvent, the product is the corresponding ester of the carboxylic acid. Most highly preferred are ethers, especially tetrahydrofuran. When solvents are used, the amount can be up to about 100 mL per gram of the compounds of formula II, but the process is most advantageously conducted in the presence of about 1 to 30 mL per gram of the compound of formula II.

In those specific embodiments of this invention in which an ibuprofen or an ester of ibuprofen is produced, the ester may be conveniently converted to the acid (ibuprofen itself) by conventional methods of hydrolysis.

The following examples are given to illustrate the process of this invention and are not intended as a limitation thereof.

EXAMPLES

Example 1 (Comparative)

$PdCl_2$ (0.029 g, 0.16 mmol) and triphenylphosphine (0.13 g, 0.50 mmol) were charged into an autoclave (Hastelloy B, 100 mL) and the autoclave was set up in the hood. The autoclave was purged with CO (3×500 psig) and a solution of 4-isobutylstyrene (1.28 g, 8.0 mmol), $H_2O$ (1 mL), and THF (30 mL) was added. The autoclave was again purged with CO (2×500 psig) and then filled with CO (500 psig). The mixture was agitated at 50° C. and monitored by GC periodically. GC analyses at 2 h, 4 h, 6 h, 8 h, and 10 h showed 3%, 9%, 11%, 16%, and 19% conversion, respectively.

Example 2 (Comparative)

PdCl$_2$ (0.029 g, 0.16 mmol) and triphenylphosphine oxide (0.15 g, 0.54 mmol) were charged into an autoclave (Hastelloy B, 100 mL) and the autoclave was set up in the hood. A solution of 4-isobutylstyrene (1.28 g, 8.0 mmol), THF (30 mL), and H$_2$O (1 mL) was added via syringe. The autoclave was purged with CO (3×500 psig) and then filled with CO (500 psig). The mixture was agitated at 50° C. and monitored by GC periodically. GC analyses showed no reaction in 24 h.

Example 3

PdCl$_2$ (0.029 g, 0.16 mmol) and Ph$_3$P/Ph$_3$PO (85:15, 0.14 g, 0.53 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added. The autoclave was purged with CO (3×500 psig) and then filled with CO (500 psig). The mixture was agitated at 50° C. and monitored by GC periodically. GC analyses at 2 h, 4 h, 6 h, 8 h, 10 h, 22 h, and 46 h showed 8%, 17%, 24%, 32%, 40%, 77%, and 98% conversion, respectively. Branched/linear ratio was 98:2.

Example 4

PdCl$_2$ (0.029 g, 0.16 mmol) and Ph$_3$P/Ph$_3$PO (50:50, 0.14 g, 0.52 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added. The autoclave was purged with CO (3×500 psig) and then filled with CO (500 psig). The mixture was agitated at 50° C. and monitored by GC periodically. GC analyses at 2 h, 3 h, 4 h, 5 h, 6 h, 8 h, 10 h, and 23 h showed 34%, 50%, 60%, 69%, 77%, 89%, 95%, and 100% conversion, respectively. Branched/linear ratio was 100:0.

Example 5 (Comparative)

PdCl$_2$ (0.029 g, 0.16 mmol) and CyPh$_2$P (0.13 g, 0.50 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added. The autoclave was purged with CO (3×500 psig) and then filled with CO (500 psig). The mixture was agitated at 50° C. and monitored by GC periodically. GC analyses at 2 h, 4 h, 6 h, 8 h, 10 h, 24 h, and 48 h showed 2%, 5%, 8%, 14%, 18%, 42%, and 78% conversion, respectively. Branched/linear ratio was approximately 250:1.

Example 6

PdCl$_2$ (0.029 g, 0.16 mmol) and CyPh$_2$P/Cyph$_2$PO (85:15, 0.14 g, 0.53 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added. The autoclave was purged with CO (3×500 psig) and then filled with CO (500 psig). The mixture was agitated at 50° C. and monitored by GC periodically. GC analyses at 2 h, 4 h, 6 h, 8 h, 10 h, and 22 h showed 3%, 8%, 13%, 19%, 24%, and 53% conversion, respectively.

Example 7

PdCl$_2$ (0.029 g, 0.16 mmol) and CyPh$_2$P/Cyph$_2$PO (50:50, 0.14 g, 0.50 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added via syringe. The autoclave was purged with CO (3×500 psig) and then filled with CO (500 psig). The mixture was agitated at 50° C. and monitored by GC periodically. GC analyses at 2 h, 4 h, 6 h, 7 h, 8 h, and 10 h showed 38%, 64%, 84%, 91%, 96%, and 100% conversion, respectively. Branched/linear ratio was 100:0.

Example 8 (Comparative)

PdCl$_2$ (0.029 g, 0.16 mmol) and EtPh$_2$P (0.11 g, 0.49 mmol) were charged into an autoclave (Hastelloy B, 100 mL) in a drybox and the autoclave was set up in the hood. THF (30 mL), 4-isobutylstyrene (1.28 g, 8.0 mmol), and H$_2$O (1 mL) were added via syringe. The autoclave was purged with CO (3×500 psig) and then filled with CO (500 psig). The mixture was agitated at 50° C. and monitored by GC periodically. GC analyses at 2 h, 4 h, 6 h, and 8 h showed no reaction.

Example 9

PdCl$_2$ (0.029 g, 0.16 mmol), EtPh$_2$P (0.053 g, 0.25 mmol), and EtPh$_2$PO (0.057 g, 0.25 mmol) were charged into an autoclave (Hastelloy B, 100 mL) in a drybox and the autoclave was set up in the hood. THF (30 mL), 4-isobutylstyrene (1.28 g, 8.0 mmol), and H$_2$O (1 mL) were added via syringe. The autoclave was purged with CO (3×500 psig) and then filled with CO (500 psig). The mixture was agitated at 50° C. and monitored by GC periodically. GC analyses at 2 h, 4 h, 6 h, and 8 h showed no reaction.

Example 10

The mixture from Example 8 was agitated at 90° C. and monitored by GC. GC analyses at 14 h and 21 h showed 59% and 79% conversion. Branched/linear ratio was 68:32.

Example 11

The mixture from Example 9 was agitated at 90° C. for 14 h. GC analysis showed the complete conversion. Branched/linear ratio was 88:12.

Example 12 (Comparative)

PdCl$_2$ (0.029 g, 0.16 mmol) and triphenylphosphine (0.13 g, 0.50 mmol) were charged into an autoclave (Hastelloy B, 100 mL). The autoclave was purged with CO and a solution of 4-isobutylstyrene (1.28 g, 8.0 mmol), HCl$_{(aq)}$ (10%, 1 mL), and THF (30 mL) was added. The autoclave was again purged with CO and then filled with CO (500 psig). The mixture was agitated at 50° C. and monitored by GC periodically. GC analyses at 2 h, 4 h, 6 h, 7 h, 8 h, 10 h, and 20 h showed 8%, 20%, 34%, 45%, 56%, and 100% conversion, respectively. The reactor was cooled to room temperature and CO pressure was released. GC analysis indicated that the branched/linear ratio was 98:2.

Example 13

PdCl$_2$ (0.029 g, 0.16 mmol) and Ph$_3$P/Ph$_3$PO (50:50, 0.14 g, 0.52 mmol) were charged into an autoclave (Hastelloy B, 100 mL) in a drybox and the autoclave was set up in the hood. THF (30 mL), 4-isobutylstyrene (1.28 g, 8.0 mmol), and HCl$_{(aq)}$ (10%, 1 mL) were added via syringe. The autoclave was purged with CO (3×500 psig) and then filled with CO (500 psig). The mixture was agitated at 50° C. and monitored by GC periodically. GC analyses at 2 h, 3 h, 4 h, and 5 h showed 54%, 74%, 91%, and 100% conversion, respectively. Branched/linear ratio was 100:0.

Example 14 (Comparative)

PdCl$_2$ (0.029 g, 0.16 mmol), CuCl$_2$ (0.050 g, 0.37 mmol), and triphenylphosphine (0.13 g, 0.50 mmol) were charged into an autoclave (Hastelloy B, 100 mL). The autoclave was set up in the hood and purged with CO. THF (30 mL), 4-isobutylstyrene (1.28 g, 8.0 mmol), and HCl$_{(aq)}$ (10%, 1 mL) were added via syringe. The autoclave was again purged with CO and then filled with CO (500 psig). The mixture was agitated at 50° C. and monitored by GC periodically. GC analyses at 2 h, 4 h, and 6 h showed 36%, 72%, and 100% conversion, respectively. The reactor was cooled to room temperature and CO pressure was released. GC analysis indicated 100% conversion of IBS to ibuprofen. No linear product was found. Standard workup gave a white solid (1.6 g, 97%): mp 73°–75° C.; $^1$H NMR δ 7.22 (d, 2H, J=8.0 Hz, o-CH), 7.10 (d, 2H, J=8.0 Hz, m-CH), 3.70 (q, 1H, J=7.3 Hz, CHCOOH), 2.44 (d, 2H, J=7.1 Hz, CH$_2$CH), 1.83 (m, 1H, CH$_2$CH), 1.50 (d, 3H, J=7.3 Hz, CH$_3$CHCOOH), 0.90 (d, 6H, J=7.1 Hz, gem-CH$_3$); $^{13}$C NMR δ 18.5, 22.9, 30.6, 45.4, 45.5, 127.7, 129.8, 137.4, 141.3, 181.7.

Example 15

PdCl$_2$ (0.029 g, 0.16 mmol), CuCl$_2$ (0.050 g, 0.37 mmol), and Ph$_3$P/Ph$_3$PO (85:15, 0.14 g, 0.51 mmol) were charged into an autoclave (Hastelloy B, 100 mL) in a drybox and the autoclave was set up in the hood. THF (30 mL), 4-isobutylstyrene (1.28 g, 8.0 mmol), and HCl$_{(aq)}$ (10%, 1 mL) were added via syringe. The autoclave was purged with CO (3×500 psig) and then filled with CO (500 psig). The mixture was agitated at 50° C. and monitored by GC periodically. GC analyses at 2 h, 4 h, and 5 h showed 48%, 88%, and 100% conversion, respectively. Branched/linear ratio was 100:0.

Example 16 (Comparative)

PdCl$_2$ (0.029 g, 0.16 mmol) and CuCl$_2$ (0.050 g, 0.37 mmol) were charged into an autoclave (Hastelloy B, 100 mL) under nitrogen. A solution of triphenylphosphine (0.13 g, 0.50 mmol), 4-isobutylstyrene (1.28 g, 8.0 mmol), MeOH (1 mL), and methyl ethyl ketone (30 mL) was added via syringe. The autoclave was purged with CO (3×500 psig) and then filled with CO (500 psig). The mixture was agitated at 50° C. and monitored by GC periodically. GC analyses at 2 h, 4 h, 6 h, 8 h, and 22 h showed 2%, 23%, 51%, 73%, and 100% conversion, respectively. The reaction mixture contained methyl 2-(4-isobutylphenyl)propionate and methyl 3-(4-isobutylphenyl)propionate in a 98:2 ratio.

Example 17

PdCl$_2$ (0.029 g, 0.16 mmol), CuCl$_2$ (0.050 g, 0.37 mmol), Ph$_3$P (0.13 g, 0.50 mmol), Ph$_3$PO (0.14 g, 0.49 mmol), THF (degassed, 30 mL), MeOH (1 mL), and 4-isobutylstyrene (1.28 g, 8.0 mmol) were loaded to an autoclave (Hastelloy C, 100-mL) and the autoclave was set up in the hood. The autoclave was purged with CO (3×500 psig) and then pressurized with CO (500 psig). The reactor was agitated at 50° C. and monitored by GC. GC analyses at 2 h, 4 h, 6 h, 8 h, and 10 h showed 14%, 41%, 73%, 92%, and 100% conversion. Branched/linear ratio was approximately 200:1. The reactor was cooled to room temperature and CO pressure was released. H$_2$O (20 mL) was added and the product was extracted with hexane (3×50 mL). The combined hexane extracts was dried (MgSO$_4$) and was concentrated by rotary evaporation. The resulting residue was chromatographed on a short column (silica gel, eluted with hexanes and 5:1 hexanes/EtOAc) to give a colorless liquid (1.56 g, 89%). GC analysis showed o-PME (2.3%), p-PME (96.8%), and LME (0.8%). PME: $^1$H NMR δ 7.20 (d, 2H, J=8.0 Hz, o-CH), 7.10 (d, 2H, J= 8.0 Hz, m-CH), 3.70 (q, 1H, J=7.1 Hz, CHCOOH), 3.66 (s, 3H, COOCH$_3$), 2.44 (d, 2H, J=7.1 Hz, CH$_2$CH), 1.84 (m, 1H, CH$_2$CH), 1.49 (d, 3H, J=7.1 Hz, CH$_3$CHCOOH), 0.90 (d, 6H, J=7.1 Hz, gem-CH$_3$); $^{13}$C NMR δ 19.1, 22.8, 30.6, 45.4, 45.5, 52.4, 127.6, 129.8, 138.2, 141.0, 175.6.

Example 18 (Comparative)

PdCl$_2$ (0.029 g, 0.16 mmol) and Ph$_3$P (0.13 g, 0.50 mmol) were charged into an autoclave (Hastelloy B, 100 mL) in a drybox and the autoclave was set up in the hood. A solution of 4-isobutylstyrene (1.28 g, 8.0 mmol), MeOH (1 mL), and MEK (30 mL) was added via syringe. The autoclave was purged with CO (3×500 psig) and then filled with CO (500 psig). The mixture was agitated at 50° C. and monitored by GC periodically. GC analyses at 2 h, 4 h, 6 h, 8 h, and 22 h showed 0%, 2%, 6%, 11%, and 76% conversion of IBS to ester, respectively. Branched/linear ratio was 97:3.

Example 19

PdCl$_2$ (0.029 g, 0.16 mmol) and Ph$_3$P/Ph$_3$PO (50:50, 0.13 g, 0.50 mmol) were charged into an autoclave (Hastelloy B, 100 mL) in a drybox and the autoclave was set up in the hood. A solution of 4-isobutylstyrene (1.28 g, 8.0 mmol), MeOH (1 mL), and MEK (30 mL) was added via syringe. The autoclave was purged with CO (3×500 psig) and then filled with CO (500 psig). The mixture was agitated at 50° C. and monitored by GC periodically. GC analyses at 2 h, 4 h, 6 h, 8 h, and 23 h showed 9%, 26%, 42%, 58%, and 99% conversion, respectively. Branched/linear ratio was approximately 200:1.

Example 20

PdCl$_2$ (0.029 g, 0.16 mmol) and Ph$_3$P/Ph$_3$PS (50:50, 0.14 g, 0.50 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added. The autoclave was purged with CO (3×500 psig) and then filled with CO (500 psig). The mixture was agitated at 50° C. and monitored by GC periodically. GC analysis at 2 h, 4 h, 6 h, 8 h, 10 h, and 23 h showed 21%, 41%, 53%, 65%, 76%, and 97% conversion, respectively. Branched/linear ratio was 100:0.

Example 21

PdCl$_2$ (0.029 g, 0.16 mmol), Ph$_3$P (0.065 g, 0.25 mmol), and Ph$_3$PSe (0.085 g, 0.25 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added. The autoclave was purged with CO (3×500 psig) and then filled with CO (500 psig). The mixture was agitated at 50° C. and monitored by GC periodically. GC analysis at 2 h, 4 h, 6 h, 8 h, 10 h, and 70 h showed 8%, 12%, 21%, 26%, 31%, and 73% conversion, respectively. Branched/linear ratio was approximately 200:1.

Example 22 (Comparative)

PdCl$_2$ (0.029 g, 0.16 mmol) and 1,3-bis(diphenylphosphino)propane (0.075 g, 0.18 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added via syringe. The autoclave was purged with CO (3×500 psig) and then filled with CO (500 psig). The mixture was agitated at 50° C. for 21 h. GC analysis indicated no reaction.

Example 23

PdCl$_2$ (0.029 g, 0.16 mmol) and 1,3-bis(diphenylphosphino)propane monoxide (0.077 g, 0.18 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added via syringe. The autoclave was purged with CO (3×500 psig) and then filled with CO (500 psig). The mixture was agitated at 50° C. and monitored by GC periodically. GC analyses at 2 h, 4 h, 6 h, 8 h, 10 h, and 23 h showed 7%, 13%, 22%, 27%, 34%, and 68% conversion, respectively. Branched/linear ratio was 100:0.

Example 24

The mixture from Example 22 was agitated at 80° C. and monitored by GC periodically. GC analyses at 2 h, 3 h, 4 h, 6 h and 9 h showed 12%, 16%, 20%, 25%, and 30% conversion, respectively. Branched/linear ratio was 32:68.

Example 25 (Comparative)

PdCl$_2$ (0.029 g, 0.16 mmol) and 1,3-bis(diphenylphosphino)propane monoxide (0.077 g, 0.18 mmol) were charged into an autoclave (Hastelloy B, 100 mL) in a drybox and the autoclave was set up in the hood. A solution of 4-isobutylstyrene (1.28 g, 8.0 mmol), H$_2$O (1 mL), and THF (30 mL) was added via syringe. The autoclave was purged with CO (3×500 psig) and then filled with CO (500 psig). The mixture was agitated at 80° C. and monitored by GC periodically. GC analyses at 2 h, 3 h, 4 h, and 6 h showed 78%, 92%, 95%, and 98% conversion, respectively. Branched/linear ratio was 98:2.

TABLE 1

A Comparison of the Rates of the Catalytic Hydrocarboxylation of IBS Phosphine Oxides

| Run | Catalyst | R$_3$P/R$_3$PO | % Conversion of Substrate to Product | | | | |
|---|---|---|---|---|---|---|---|
| | | | 2 h | 4 h | 6 h | 8 h | 10 h |
| 1 | PdCl$_2$/Ph$_3$P | 100:0 | 3 | 9 | 11 | 16 | 19 |
| 2 | PdCl$_2$/Ph$_3$P | 0:100 | 0 | 0 | 0 | 0 | 0 |
| 3 | PdCl$_2$/Ph$_3$P | 85:15 | 8 | 17 | 24 | 32 | 40 |
| 4 | PdCl$_2$/Ph$_3$P | 50:50 | 34 | 60 | 77 | 89 | 95 |
| 5 | PdCl$_2$/CyPh$_2$P | 100:0 | 2 | 5 | 8 | 14 | 18 |
| 6 | PdCl$_2$/CyPh$_2$P | 85:15 | 3 | 8 | 13 | 19 | 24 |
| 7 | PdCl$_2$/CyPh$_2$P | 50:50 | 38 | 64 | 84 | 96 | 100 |
| 8 | PdCl$_2$/EtPh$_2$P | 100:0 | 0 | 0 | 0 | 0 | 0 |
| 9 | PdCl$_2$/EtPh$_2$P | 50:50 | 0 | 0 | 0 | 0 | 0 |
| 10 | PdCl$_2$/EtPh$_2$P,90° C. | 100:0 | 59, 14 h | 79, 21 h | B/L = 68:32 | | |
| 11 | PdCl$_2$/EtPh$_2$P,90° C. | 50:50 | 100, 14 h | | B/L = 88:12 | | |
| 12 | PdCl$_2$/10% HCl/Ph$_3$P | 100:0 | 8 | 20 | 34 | 45 | 56 |
| 13 | PdCl$_2$/10% HCl/Ph$_3$P | 50:50 | 54 | 91 | 100, 5 h | | |
| 14 | PdCl$_2$/CuCl$_2$/10% HCl/Ph$_3$P | 100:0 | 36 | 72 | 100 | | |
| 15 | PdCl$_2$/CuCl$_2$/10% HCl/Ph$_3$P | 85:15 | 48 | 88 | 100, 5 h | | |

Conditions:
P$_{CO}$ = 500 psig, Temperature = 50° C, Ligand = R$_3$P/R$_3$PO (3 equiv)
Solvent = THF/H$_2$O (30:1), Substrate/catalyst = 50

TABLE 2

A Comparison of the Rates of the Catalytic Hydrocarbomethoxylation of IBS Phosphine Oxides

| Run | Catalyst | R$_3$P/R$_3$PO | % Conversion of Substrate to Product | | | |
|---|---|---|---|---|---|---|
| | | | 2 h | 4 h | 6 h | 8 h |
| 16 | PdCl$_2$/CuCl$_2$/Ph$_3$P,In situ | 100:0 | 2 | 23 | 51 | 73 |
| 17[1] | PdCl$_2$/CuCl$_2$/Ph$_3$P,In | 50:50 | 14 | 41 | 73 | 92 |

TABLE 2-continued

A Comparison of the Rates of the Catalytic
Hydrocarbomethoxylation of IBS
Phosphine Oxides

| | | | % Conversion of Substrate to Product | | | |
|---|---|---|---|---|---|---|
| Run | Catalyst | $R_3P/$ $R_3PO$ | 2 h | 4 h | 6 h | 8 h |
| | situ | | | | | |
| 18 | $PdCl_2/Ph_3P$ | 100:0 | 0 | 2 | 6 | 11 |
| $19^2$ | $PdCl_2/Ph_3P$ | 50:50 | 9 | 26 | 42 | 58 |

Conditions:
$P_{CO}$ = 500 psig, Temperature = 50° C., Ligand = $Ph_3P$ (3 eq), Solvent = MEK/MeOH (30:1), Substrate/catalyst = 50.
[1]Ligand = $Ph_3P$(3 eq)/$Ph_3PO$(3 eq), Solvent = THF/MeOH (30:1).?
[2]Ligand = $Ph_3P/Ph_3PO$ (total = 3 eq).

TABLE 3

A Comparison of the Rates of the Catalytic
Hydrocarboxylation of IBS
Phosphorus (V) Ligands

| | | | % Conversion of Substrate to Product | | | | |
|---|---|---|---|---|---|---|---|
| Run | Catalyst | $R_3P/R_3PY$ | 2 h | 4 h | 6 h | 8 h | 10 h |
| 1 | $PdCl_2/Ph_3P$ | 100:0 | 3 | 9 | 11 | 16 | 19 |
| 4 | $PdCl_2/Ph_3P$ | 50:50, Y = O | 34 | 66 | 77 | 89 | 95 |
| 20 | $PdCl_2/Ph_3P$ | 50:50, Y = S | 21 | 41 | 53 | 65 | 76 |
| 21 | $PdCl_2/Ph_3P$ | 50:50, Y = Se | 8 | 12 | 21 | 26 | 31 |

Conditions:
$P_{CO}$ = 500 psig, Temperature = 50° C., Ligand = $R_3P/R_3PY$ (3 equiv), Solvent = THF/$H_2O$ (30:1), Substrate/catalyst = 50.

TABLE 4

A Comparison of the Rate of the Hydrocarboxylation of IBS
Bisphosphine Monoxide

| | | | Temp | % Conversion of Substrate to Product | | | | |
|---|---|---|---|---|---|---|---|---|
| Run | Catalyst | Phosphine | (°C.) | 2 h | 4 h | 6 h | 8 h | 10 h |
| 22 | $PdCl_2$ | dppp | 50 | 0 | 0 | 0 | 0 | 0 |
| 23 | $PdCl_2$ | dpppO | 50 | 7 | 13 | 22 | 27 | 34 |

| | | | Temp | % Conversion of Substrate to Product | | | | |
|---|---|---|---|---|---|---|---|---|
| Run | Catalyst | Phosphine | (°C.) | 2 h | 3 h | 4 h | 6 h | 9 h |
| 24 | $PdCl_2$ | dppp | 80 | 12 | 16 | 20 | 25 | 30 |
| 25 | $PdCl_2$ | dpppO | 80 | 78 | 92 | 97 | 100 | |

Conditions:
$P_{CO}$ = 500 psig, Ligand = 3 equiv, Solvent = THF/$H_2O$ (30:1), Substrate/catalyst = 50.
dppp = 1,3-bis(diphenylphosphino)propane
dpppO = 1,3-bis(diphenylphosphino)propane monoxide It is obvious that many variations may be made in the products and processes set forth above without departing from the spirit and scope of this invention.

I claim:

1. A process for preparing an aryl-substituted aliphatic ester having the formula:

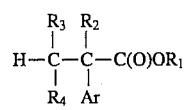

where $R_1$ is alkyl, $R_2$, $R_3$ and $R_4$ are hydrogen, alkyl, cycloalkyl, alkyl-substituted cycloalkyl, aryl either substituted or unsubstituted, alkoxy, alkylthio, heteroaryl either substituted or unsubstituted, alkanoyl, aroyl either substituted or unsubstituted, heteroarylcarbonyl either substituted or unsubstituted, trifluoromethyl or halo and Ar is unsubstituted or substituted aryl which comprises treating a compound of the formula:

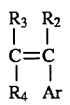

where Ar, $R_2$, $R_3$ and $R_4$ are as previously defined and a compound of the formula $R_1OH$ where $R_1$ is as previously defined with carbon monoxide at a pressure of at least about 1 atmosphere and a temperature from about 25° C. to about 200° C. in the absence of oxygen and in the presence of a catalyst that is i) a mixture of palladium(O) or the salts of palladium or a mixture of palladium(O) and the salts of palladium and the salts of copper and (ii) a ligand mixture comprising a compound of the formula $(R')_3ZY$ and a compound of the formula $(R'')_3Z$ where each R' and R" are the same or different and are alkyl, aryl or substituted aryl, and Z is any atom that has a Pauling electronegativity of between 1.9 and 2.5 and Y is a member of Group VIA of the Periodic Table of Elements.

2. A process of claim 1 wherein the palladium salt is a palladium(II) salt.

3. A process of claim 2 wherein the palladium salt is palladium(II) chloride.

4. A process of claim 1 wherein R' and R" are individually the same or different and are $C_1$ to $C_6$ alkyl, phenyl, substituted phenyl or are joined with Z to form a pyridine ring.

5. A process of claim 1 wherein R' and R" are the same and are phenyl and Z is phosphorus.

6. A process of claim 5 wherein the ligand mixture comprises triphenylphosphine and triphenylphosphine oxide.

7. A process of claim 1 wherein the treatment is carried out in the absence of water.

8. A process of claim 1 wherein the treatment is carried in an anhydrous medium.

9. A process for preparing ibuprofen which comprises carboxylating 4-isobutylstyrene with carbon monoxide in an anhydrous acidic medium containing tetrahydrofuran as a solvent and about 3–24 mols of anhydrous methanol or ethanol per mol of said 4-isobutylstyrene at a temperature in the range of about 25°–120° C. and a carbon monoxide pressure in the range of about 400–800 psig in the presence of (a) a mixture of a palladium(II) compound and optionally a copper (II) compound and (b) a mixture of ligands of the formulas $(R')_3ZY$ and $(R'')_3Z$ where R' and R" are $C_1$ to $C_6$ alkyl, phenyl or substituted phenyl, Z is phosphorus, Y is oxygen and in the presence of an amount of hydrogen chloride such as to provide an amount up to about 10 mols of hydrogen chloride per mol of 4-isobutylstyrene.

10. A process of claim 9 wherein the palladium(II) compound is palladium(II) chloride the copper (II) compound is copper(II) chloride and the ligand mixture is equal parts of triphenylphosphine and triphenylphosphine oxide.

11. A process for preparing ibuprofen which comprises carboxylating 4-isobutylstyrene with carbon monoxide in an anhydrous neutral medium containing tetrahydrofuran as a solvent and about 3–24 mols of an aliphatic alcohol per mol of said isobutylstyrene and no added acid at a temperature in the range of about 50°–100° C. and a carbon monoxide pressure in the range of about 400–800 psig, in the presence of (a) a mixture of palladium(II) inorganic salt and optionally a copper(II) inorganic salt, and (b) a mixture of ligands of the formulas $(R')_3ZY$ and $(R'')_3Z$ where R' and R" are $C_1$ to $C_6$ alkyl, phenyl or substituted phenyl and Z is phosphorus and Y is oxygen.

12. A process for preparing ibuprofen which comprises carboxylating 4-isobutylstyrene with carbon monoxide in an aqueous acidic medium containing tetrahydrofuran as a solvent and about 3–24 mols of anhydrous methanol or ethanol per mol of said 4-isobutylstyrene at a temperature in the range of about 25°–120° C. and a carbon monoxide pressure in the range of about 400–800 psig in the presence of (a) a mixture of a palladium(II) compound and optionally a copper (II) compound and (b) a mixture of ligands of the formulas $(R')_3ZY$ and $(R'')_3Z$ where R' and R" are $C_1$ to $C_6$ alkyl, phenyl or substituted phenyl, Z is phosphorus, Y is oxygen and in the presence of an amount of hydrogen chloride such as to provide an amount up to about 10 mols of hydrogen chloride per mol of 4-isobutylstyrene.

13. A process for preparing ibuprofen which comprises carboxylating 4-isobutylstyrene with carbon monoxide in an aqueous neutral medium containing tetrahydrofuran as a solvent and about 3–24 mols of an aliphatic alcohol per mol of said isobutylstyrene and no added acid at a temperature in the range of about 50°–100° C. and a carbon monoxide pressure in the range of about 400–800 psig, in the presence of (a) a mixture of palladium(II) inorganic salt and optionally a copper(II) inorganic salt, and (b) a mixture of ligands of the formulas $(R')_3ZY$ and $(R'')_3Z$ where R' and R" are $C_1$ to $C_6$ alkyl, phenyl or substituted phenyl and Z is phosphorus and Y is oxygen.

* * * * *